United States Patent [19]

Lamberti et al.

[11] 4,056,567

[45] Nov. 1, 1977

[54] CHEMICAL PROCESSES FOR PREPARING CITRIC ACID

[75] Inventors: Vincent Lamberti, Upper Saddle River; Eddie N. Gutierrez, Fort Lee, both of N.J.

[73] Assignee: Lever Brothers Company, New York, N.Y.

[21] Appl. No.: 664,449

[22] Filed: Mar. 8, 1976

[51] Int. Cl.$^2$ .............................................. C07C 59/16
[52] U.S. Cl. .................................................. 260/535 P
[58] Field of Search .................................... 260/535 P

[56] References Cited

U.S. PATENT DOCUMENTS

| | | | |
|---|---|---|---|
| 3,128,287 | 4/1964 | Berg | 260/346.8 R |
| 3,769,337 | 10/1973 | Wiegand | 260/535 P |
| 3,810,931 | 5/1974 | Guthrie et al. | 260/535 P |

*Primary Examiner*—Paul J. Killos
*Attorney, Agent, or Firm*—James J. Farrell; Kenneth F. Dusyn; Melvin H. Kurtz

[57] ABSTRACT

Novel chemical processes are disclosed for the conversion of cis-aconitic acid, trans-aconitic acid, isocitric acid, alloisocitric acid and mixtures thereof into citric acid. The processes comprise heating selected alkaline earth metal salts of the aconitic and isocitric acids in an aqueous medium in the presence of alkali metal hydroxides or, preferably, selected alkaline earth metal hydroxides at elevated temperatures to produce the corresponding salts of citric acid.

17 Claims, No Drawings

CHEMICAL PROCESSES FOR PREPARING CITRIC ACID

BACKGROUND OF THE INVENTION

Hydration of simple double bond functions in organic molecules to form alcohols is well known in the art and is readily accomplished by acid catalysis. Hydration of symmetrical substituted molecules such as α, β-unsaturated dicarboxylic acids is relatively more difficult and generally requires special reaction conditions. The acid catalyzed hydrations of maleic acid and fumaric acid to produce malic acid are well known examples of such processes.

In contrast to maleic and fumaric acid, α, β-unsaturated dicarboxylic acids containing additional carboxyl groups one or more carbon atoms away from the double bond, such as aconitic acid, are very resistant to acid catalyzed hydration, and under such conditions either preferentially undergo decarboxylation to produce a mixture of dicarboxylic acids or do not react at all.

In addition to the acid catalysts used for hydrating simple α, β-unsaturated dicarboxylic acids such as maleic and fumaric acids the art also recognizes the use of alkali metal hydroxides for this purpose as taught by F. Loydl, Ann. 192 80 (1878) and Van't Hoff, Jr., Ber. 18 2713 (1885) which are incorporated herein by reference. R. Berg, in U.S. Pat. No. 3,128,287, particularly column 1, lines 68–72 and column 2, lines 1–2, which is also incorporated herein by reference, teaches that maleic acid is converted into about an equal mixture of malic acid and oxydisuccinic acid by heating with excess calcium hydroxide or magnesium hydroxide in aqueous medium. The Berg reference also teaches that when strontium hydroxide and barium hydroxide are utilized in his process, the maleic acid is converted almost quantitatively into malic acid. Ger. Offen. 2,220,295 discloses the reaction of aconitic acid with glycolic acid in the presence of excess calcium hydroxide to form an addition product. However, there appears to be no references in the literature regarding the behavior of aconitic acid towards the action of excess aqueous alkali in the absence of other reagents. We have found that heating an aqueous solution of aconitic acid with an excess of an alkali metal hydroxide such as potassium hydroxide cleaves the molcule to produce a mixture of the corresponding alkali metal salts of acetic acid and itaconic acid as well as other degradation products. This cleavage can be explained in part in terms of a reverse aldol reaction with the intermediate hydration product as has been described for the hydrolytic cleavage of double bonds in general by Patai, in "The Chemistry of the Alkenes," Interscience Publishers, 1964, page 548, which is incorporated herein by reference.

In summary, neither the acid nor alkaline catalyzed hydration of aconitic acid to form citric acid and/or isocitric acid or their salts has been taught by the prior art. If a suitable hydration process could be devised for aconitic acid, it would afford a new and relatively simple route to citric acid and/or isocitric acid which have well known commercial uses such as, but not limited to, food acidulants and flavors and metal cleaners.

SUMMARY OF THE INVENTION

It is an object of this invention to provide an efficient process for converting cis- and trans-aconitic acids into citric acid.

It is a further object of this invention to provide an efficient process for converting precursors of aconitic acid, such as isocitric acid and alloisocitric acid and the corresponding lactones thereof, into citric acid.

It has now been discovered that the calcium, magnesium or strontium salts of a tricarboxylic acid selected from the group consisting of cis-aconitic acid, trans-aconitic acid, isocitric acid, alloisocitric acid and mixtures thereof are converted into the corresponding salt or salts of citric acid by a novel process comprising heating said salts in aqueous medium in the presence of an alkali metal hydroxide or, preferably, selected alkaline earth metal hydroxides at a temperature of at least about 160° C. Isolation of citric acid from the reaction mixtures is then carried out by conventional means well recognized in the art.

DETAILED DESCRIPTION OF THE INVENTION

In accordance with the first embodiment of this invention it has been discovered that certain alkaline earth metal salts (namely, the calcium, magnesium and strontium salts) of cis-aconitic acid, trans-aconitic acid and mixtures thereof, can be readily hydrated to form the corresponding salts of citric acid. This is accomplished by heating these tricarboxylic acids to at least about 160° C in aqueous medium in the presence of an alkali metal hydroxide or, preferably, an alkaline earth metal hydroxide selected from the group of calcium hydroxide, magnesium hydroxide and strontium hydroxide and mixtures thereof. The reaction may be represented as follows for the preferred mode:

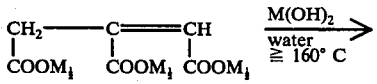

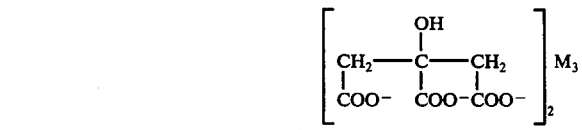

wherein M is an alkaline earth metal cation selected from the group consisting of Ca++, Mg++, Sr++ and mixtures thereof. For the purposes of this specification it will be understood that the term salts shall include chelate structures as well as the simple ionic structures depicted above.

The process of the invention is surprisingly selective in that the only hydration product is citric acid (i.e. in the form of the alkaline earth metal salt). Also, very little decomposition of either the hydration product or the aconitic acid occurs under the preferred conditions of the process. Isocitric acid, which theoretically could be formed at the same time, is not found in the reaction mixture. Any isocitric acid formed apparently undergoes an isomerization reaction to produce citric acid as will be described in more detail in the second embodiment of this invention.

The most preferred alkaline earth metal metal salts of aconitic acid in the process are the calcium salts. Likewise, the most preferred alkaline earth metal hydroxide is calcium hydroxide. The barium salt of aconitic acid and barium hydroxide have been found to be inoperative in the process in the absence of the other alkaline earth metal cations. When using either Ca(OH)$_2$ or Sr(OH)$_2$, the amount of aklaline earth metal hydroxide used in the reaction as indicated by pH (measured at room temperature) is preferably the amount sufficient to bring the pH of the aqueous reactant mixture into the range of from about 11.3 to about 12.5 and most preferably from about 11.6 to about 12.0. When $Mg(OH)_2$ is utilized, the amount necessary is that required to bring the pH (measured at room temperature) into the range of from about 8.5 to about 9.0 and preferably about 9.0. When mixtures of the alkaline earth metal hydroxides are utilized, or when alkali metal hydroxides are present, the optimum pH is in the range of about 11.3 to about 12.5. It should be recognized that the particular pH at which the reaction occurs is not critical except that in order to obtain optimum reaction rates and to avoid degradation reactions the pH range referred to above is preferred. Certainly one skilled in the art would only need to be nominal experimentation to avoid those pH's at which the citrate salt would be forming at an impractically slow rate or was undergoing extensive degradation reactions after formation. It will also be apparent that the corresponding alkaline earth metal oxides may also be used in the process inasmuch as the reaction medium contains water which will immediately convert the oxides into the desired hydroxide form.

Alkali metal hydroxides such as sodium hydroxide, potassium hydroxide and lithium hydroxide may be used in partial or complete replacement of the excess alkaline earth metal hydroxide utilized to attain an alkaline pH. Use of the alkali metal hydroxides is a less preferred mode, however, since the alkali metal hydroxides promote degradation reactions. If, in addition to replacing the excess alkaline earth metal hydroxide with an alkali metal hydroxide, one also replaces the alkaline earth metal salts of the aconitic acid completely with the alkali metal salts of aconitic acid, then only degradation reactions occur and no citric acid is found in the reaction mixture. The degradation reactions presumably arise at least in part from a reverse aldol reaction of the primary hydration product(s) as discussed previously. The presence of some alkaline earth metal cation either in the form of the salt of the aconitic acid or in the form of the alkaline earth metal hydroxide is an important feature of the process.

It will be recognized that another process mode is to treat the alkali metal salts of aconitic acid with one or more of the selected alkaline earth metal hydroxides. Due to the solubility characteristics of the various salts possible, the calcium, magnesium or strontium salts, respectively, of aconitic acid will be formed to a significant extent in the mixture with the simultaneous formation of the corresponding alkali metal hydroxide. Accordingly, it will be within the scope of this invention to produce the desired alkaline earth metal salts of aconitic acid by such an indirect route.

The process of the invention is carried out either continuously or batchwise under pressure at elevated temperatures of at least 160° C and preferably in the range from about 160° C to about 300° C and most preferably at about 175° C to about 250° C. The pressure under which the reaction takes place is not critical to the process provided the temperature conditions are met. The pressure will normally correspond approximately to the vapor pressure of the aqueous medium being employed at the temperature being utilized for the reaction. The pressure may also be enhanced by inclusion of relatively volatile inert organic solvents in the reaction medium or by pre-pressurizing the autoclave with an inert gas such as nitrogen prior to heating the reaction mixture to reaction temperature. Again, as stated previously, the important parameter is the temperature of the reaction and not the pressure.

Standard autoclave equipment may be used in carrying out the process of the invention. The alkaline nature of the process is advantageous in that it enables one to utilize steel and stainless steel as materials of construction for the autoclave without the need for resorting to more expensive materials of construction.

The alkaline earth metal salt of the cis-aconitic acid or trans-aconitic acid in the process of the invention may be completely dissolved, partially dissolved or merely dispersed in the water medium at reaction temperature. The amount of water is not critical but should be sufficient to provide the water of hydration as well as excess water to allow the reaction medium to be stirred readily and thereby facilitate heat transfer from the reactor or heat exchanger into the reaction medium. A convenient range of the molar ratio of water to the alkaline earth metal salt of aconitic acid present in the reaction mixture is from about 5 to 1 to about 500 to 1.

Mixed reaction media containing water and an inert organic liquid or mixture of liquids may also be used as the aqueous medium for the reaction. One inert organic liquid which does not interfere with the reaction, for example, is t-butanol which may be employed in mixtures with water as the reaction medium. When a mixed reaction media is utilized the major criteria is that sufficient water must be present in the original medium or must be generated by the reactant as for example during isomerization to hydrate double bonds present initially or formed during reaction and can be readily determined by one skilled in the art.

The reaction time for the process is in the range of about a few minutes to about 8 hours depending on the temperature of the reaction and the desired degree of conversion. For example, at 225° C, 2 hours is sufficient to convert over 90% of the calcium salt of aconitic acid into the corresponding salt of citric acid. In general, long reaction times are less desirable since under the reaction conditions a slow decomposition of the citrate salt produced may occur especially if alkali metal cation species are present in the reaction mixture.

In the second embodiment of the invention, the calcium, magnesium and strontium salts of the tricarboxylic acids: isocitric acid, alloisocitric acid and mixtures thereof are readily isomerized to the corresponding salts of citric acid by using the identical conditions described above for converting aconitic acid into citric acid. While there is no wish to be limited to the following explanation, it is believed that under the conditions of the process of the invention, the alkaline earth metal salts of isocitric acid and alloisocitric acid undergo a dehydration reaction to produce cis- and/or trans-aconitic acid which, in turn, rehydrate to form the more stable alkaline earth metal salt of citric acid. It appears that the high stability of the alkaline earth metal salt or chelate of citric acid relative to the stability of the alkaline earth metal salt or chelate of isocitric acid and/or alloisocitric acid is the driving force for the reaction. Under the preferred reaction conditions the isomerization reaction may be represented as follows:

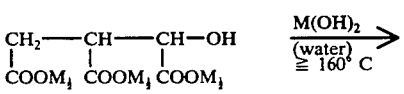

-continued

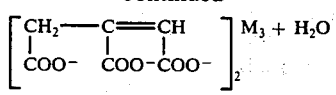

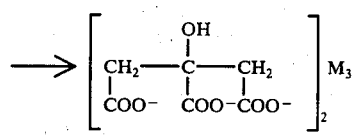

wherein M is Ca++, Mg++ or Sr++ and mixtures thereof.

The general and preferred conditions i.e. temperature, pH, aqueous medium, water ratio, reaction time, etc. of the process of the second embodiment of invention, which utilizes the calcium, magnesium or strontium salts of isocitric acid or alloisocitric acid or mixtures thereof, are identical to those previously described for the first embodiment, which utilizes the corresponding salts of cis- and trans-aconitic acid. Thus, as explained above, the alkali metal hydroxides may be substituted for part or all of the excess alkaline earth metal hydroxides utilized in the reaction. Again, however, this is a less preferred mode due to degradation reactions which are promoted by the presence of alkali metal hydroxides.

Also, any of the stereoisomeric forms i.e., d, l or dl, i.e. racemic mixtures of isocitric acid or alloisocitric acid or their lactones may be utilized in the process of the invention. It will also be apparent that any precursor compound which gives rise to isocitric acid, alloisocitric acid, cis-aconitic acid or trans-aconitic acid under the conditions of the process of the invention, can also be utilized in the process of the invention. Examples of such precursors are the hydrolyzable esters and the lactone forms of these acids.

Although aconitic acid is usually obtained from natural sources, it can be obtained synthetically by the method taught by Michael, J. pr. Chem. 1894 (ii) 49 21 and those methods described by Kirk-Othmer, Encyclopedia of Chemistry Technology, Vol. 1, p. 161, Interscience, 1947, both of which are incorporated herein by reference. Similarly, isocitric acid and alloisocitric acid can also be produced synthetically by the methods taught by Pacher and Vickery, J. Biol. Chem. 163 169 (1946) and Gawron et al., JACS 80 5856 (1958), both of which are incorporated herein by reference. Thus, the process of the invention provides completely synthetic routes to citric acid.

Isolation of citric acid from the reaction mixtures of the process of the invention as explained above is readily carried out by conventional methods known to the art. The most preferred reaction mixtures, for example, may contain in addition to the calcium salt of citric acid small amounts of the corresponding salts of the following carboxylic acids: succinic acid, acetic acid and oxalic acic. When cis- or trans-aconitic acid is used as a starting material, unreacted aconitic acid may also be present in the product unless the reaction is preferably carried out to completion. In any event, all of the possible products can be separated from each other by methods known to the art. Some of these methods are summarized briefly as follows although other methods may be used as known by the art:

1. The known method of purifying citric acid via its calcium salt is employed. This method is set forth in Kirk-Othmer, Encyclopedia of Chemical Technology, Vol. 4, pp. 12-17 Interscience, 1949, which is incorporated herein by reference. Thus, the reaction mixture obtained in the process of the invention, when the calcium salts are utilized, is first filtered to obtain a cake of the calcium salts of citric acid and the accompanying acids together with calcium hydroxide. The cake is then washed with hot water to remove the more soluble salts such as calcium acetate and calcium succinate. The cake is then treated with sulfuric acid to precipitate calcium sulfate which then, together with other insoluble calcium salts, is removed by filtration. The resulting liquid filtrate may then be treated in a variety of ways to recover pure citric acid. For example, (a) the filtrate may be subjected to ion exchange chromatography or electrodialysis using an ion exchange membrane to separate the acids directly, (b) the filtrate may be sequentially extracted, first, partially extracted with a suitable solvent such as methyl isobutyl ketone to remove undesirable carboxylic acids followed by extraction with butanol or 2-butanol to isolate the citric acid, (c) the filtrate may be extracted with a solvent such as 2-butanol to recover a crude citric acid which is then recrystallized from a suitable solvent such as a mixture of chloroform and acetone, (d) the filtrate may be concentrated and crystallized to produce a purified citric acid which, if desired, may be recrystallized again from an aqueous medium or from a suitable organic solvent such as a mixture of chloroform and acetone to produce pure citric acid, and (e) the filtrate may be concentrated and treated with a mixture of a lower alkanol such as methanol and sulfuric acid to convert all carboxylic compounds to the ester forms which can then be isolated and separated by fractional distillation.

2. In another method, the reaction mixture (Ca, Mg or Sr salts or mixtures thereof) from the process of the invention may be treated with a cation exchange resin to remove all metal ions. The eluate is then concentrated and treated in any one of the ways described above in (1a)–(1e).

3. In yet another method, the reaction product of the process of the invention may be treated with an alkali metal carbonate (e.g. sodium carbonate) to precipitate all alkaline earth metal cations as the insoluble carbonates which are then removed by filtration. The resulting filtrate containing the alkali metal salts of the carboxylic products may then be concentrated by evaporation of the water and the desired alkali metal citrate either precipitated with a water-miscible organic solvent such as for example methanol, ethanol, isopropanol and acetone as well as mixtures of such solvents or crystallized directed from the solution by cooling. Further purification of the alkali metal citrate may be accomplished by recrystallization of the salt from water alone or from mixtures of water and the aforesaid organic solvents. In general, such recrystallization will recover the alkali metal citrate in the hydrate form.

In all cases, if desired, the oxalic acid impurity may be first decomposed by addition of an oxidizing agent to the reaction mixture or using other known means before completing the purification steps outlined above.

Having thus described the invention and its several and preferred embodiments, the following are Examples representative of the invention. Modifications, of course, will occur to those skilled in the art and the invention is not limited to the Examples shown.

In the Examples below the compositions of the citric acid products are determined by NMR analysis (Varian T60 instrument) using $D_2O$ as the solvent and potassium biphthalate as the internal standard. All parts and percentages herein are by weight unless specified otherwise. All pH measurements are taken at room temperature, i.e. 25° C.

EXAMPLE 1

Trans-aconitic acid, 26.1 g (0.15 mole), is dissolved in 300 mls water. An excess of calcium hydroxide, 48 g (0.65 mole) is added. This brings the pH to 11.7 and produces a mixture of the calcium salt of trans-aconitic acid and free calcium hydroxide. The mixture is stirred and heated for 5½ hours in a Parr pressure reactor at a temperature of 200° C. The reaction mixture is then cooled, neutralized with carbon dioxide to a pH of 8.6 and mixed with 15.6 g (0.15 mole) of sodium carbonate. The resulting mixture is stirred at 50° C for 15–20 minutes and then filtered to remove the precipitated calcium carbonate. The filtrate is evaporated in vacuo to give 35 g of a solid residue containing 84.6% (79% yield) of trisodium citrate, 1.7% disodium succinate and the balance mainly water.

EXAMPLE 2

Trans-aconitic acid, 17.4 g (0.10 mole) is dissolved in 300 ml of water. An excess of calcium hydroxide 25 g (0.34 mole) is added. This brings the pH to 11.7 and produces a mixture of the calcium salt of trans-aconitic acid and free calcium hydroxide. The resulting mixture is stirred and heated for 6 hours in a Parr pressure reactor at a temperature of 200° C. The reaction mixture is then cooled, slurried with excess cation exchange resin (Permutit Q) and then poured onto a column of additional cation exchange resin. After washing the resin thoroughly with water (until the pH of the column effluent is about 7), the eluate including the washings are evaporated in vacuo to give 19 g of solid residue containing 97.3% (97% yield) of citric acid, 2.2% succinic acid and the balance, water.

EXAMPLE 3

The procedure of Example 2 is followed except that the reaction is carried out at 225° C for 2 hours. There is obtained 18.5 g of product containing 100% (96% yield) citric acid.

EXAMPLE 4

Trans-aconitic acid, 17.4 g (0.10 mole) is dissolved in 400 ml of water. An excess of calcium hydroxide, 25 g (0.34 mole), is added. This brings the pH to about 11.9 and produces a mixture of the calcium salt of trans-aconitic acid and free calcium hydroxide. The resulting mixture is stirred and heated to a temperature of 250° C over a period of 1½ hours. The heat is then shut off and the reaction mixture allowed to cool slowly over a period of about 1 hour. The reaction mixture is then stirred with excess cation exchange resin and poured onto a column of additional cation exchange resin. After washing the resin thoroughly with water, the eluate including the washings are evaporated in vacuo to give a 17.8 g residue containing 98.8% (92% yield) of citric acid and 1.2% succinic acid.

EXAMPLE 5

Cis-aconitic acid, 10.7 g (0.06 mole), is dissolved in 400 mls of water. An excess of calcium hydroxide, 20 g (0.27 mole), is added. This brings the pH to 11.7 and produces a mixture of the calcium salt of cis-aconitic acid and free calcium hydroxide. The resulting mixture is stirred and heated for 6 hours in a Parr pressure reactor at a temperature of 200° C. The reaction mixture is then cooled and mixed with 127.1 g of 21% sulfuric acid solution. After stirring the mixture for about 10 minutes, it is filtered to remove precipitated $CaSO_4$. The filtrate is then evaporated in vacuo to give 9.5 g of a solid residue containing 95% (75% yield) of citric acid and the balance, water.

EXAMPLE 6

Trans-aconitic acid, 17.4 g (0.10 mole), is dissolved in 250 ml of water. An excess of calcium hydroxide, 25 g (0.34 mole), is added. Tnis brings the pH to 11.8 and produces a mixture of the calcium salt of trans-aconitic acid and free calcium hydroxide. Additional water, 150 ml, and t-butanol, 100 ml, are then added and the resulting mixture is stirred and heated for 6 hours in a Parr pressure reactor at a temperature of 200° C. The reaction mixture is then cooled, slurried with excess cation exchange resin and poured onto a column of additional cation exchange resin. After washing the resin thoroughly with water, the eluate including the washings are evaporated in vacuo to give a 19.2 g residue containing 90.2% (90.7% yield) citric acid, 1.4% succinic acid and the balance, mainly water.

EXAMPLE 7

Trans-aconitic acid, 17.9 (0.103 mole), is dissolved in 400 mls of water. An excess of $Ca(OH)_2$, 12.3 g (0.17 mole). This brings the pH to 11.4 and produces a mixture of the calcium salt of trans-aconitic acid and free calcium hydroxide. The resulting mixture is stirred and heated for 6½ hours in a Parr pressure reactor at a temperature of 200° C. The reaction mixture is then cooled, slurried with excess cation exchange resin and then poured onto a column of additional cation exchange resin. After washing the resin thoroughly with water, the eluate including the washings are evaporated in vacuo to give 15.8 g of a residue containing 8.5% (7% yield) of citric acid, 80% of unreacted trans-aconitic acid and the balance, water.

EXAMPLE 8

Trans-aconitic acid, 17.4 g (0.10 mole), is dissolved in 500 ml of water. $Ca(OH)_2$, 11.6 g (0.16 mole), is added to bring the pH to 8.8. Next, 50% sodium hydroxide, 4.3 g (0.05 mole), is added to bring the pH to about 11.9. The resulting mixture then is stirred and heated for 2 hours in a Parr pressure reactor at a temperature of 225° C. The reaction mixture is then cooled, slurried with excess cation exchange resin and poured onto a column of additional cation exchange resin. After washing the resin thoroughly with water, the eluate including the washings are evaporated in vacuo to give 10 g of a residue containing 17% (9% yield) citric acid, 38% citraconic acid, 20% itaconic acid and the balance, mainly water.

EXAMPLE 9

Trans-aconitic acid, 10.7 g (0.06 mole), is dissolved in 300 ml of water. An excess of strontium oxide, 12.5 g (0.121 mole) mole is added. This brings the pH to 12.4 and produces a mixture of the strontium salt of trans-aconitic acid and free strontium hydroxide. The resulting mixture is then stirred and heated for 3 hours in a Parr pressure reactor at a temperature of 200° C. The reaction mixture is then cooled and mixed with 121 g of 10% sulfuric acid solution. After stirring the mixture for about 10 minutes, it is filtered to remove precipitated SrSO$_4$. The filtrate is then evaporated in vacuo to give a residue which is purified further by digesting with 100 ml acetone and refiltering to remove insolubles. The acetone filtrade is then evaporated to give an 8.8 g residue containing 54.3% (37.6% yield) of citric acid, 9.6% trans-aconitic acid, 4% succinic acid and the balance, mainly water.

EXAMPLE 10

Trans-aconitic acid, 17.4 g (0.10 mole) is dissolved in 300 mls of water. An excess of magnesium hydroxide, 25 g (0.43 mole), is added. This brings the pH to 9.0 and produces a mixture of the magnesium salt of trans-aconitic acid and free magnesium hydroxide. The resulting mixture is then stirred and heated for 6 hours in a Parr pressure reactor at a temperature of 170° C. The reaction mixture is then cooled, mixed with 143 g of 30% sulfuric acid solution and the resulting solution evaporated to dryness in vacuo. The evaporation residue is then extracted with 400 mls of acetone and the acetone extract filtered to remove MgSO$_4$. The acetone filtrate is then evaporated to give 19 g of a residue containing 47% (47% yield) of citric acid, 9% citramalic acid, 5% citraconic acid, 10% itaconic acid, 12% trans-aconitic acid and the balance, water.

EXAMPLE 11

Five grams (0.028 mole) of 97% dl-isocitric acid lactone is dissolved in 250 mls of water. An excess of calcium hydroxide, 15.0 g (0.20 mole), is added. This brings the pH to 11.9 and produces a mixture of the calcium salt of the di-isocitric acid and free calcium hydroxide. The resulting mixture is stirred and heated for 6 hours in a Parr pressure reactor at a temperature of 200° C. The reaction mixture is then cooled and mixed with 120.1 g of 16.7% sulfuric acid solution. After stirring the mixture for 10 minutes, it is filtered to remove precipitated CaSO$_4$. The filtrate is then evaporated to dryness and the resulting residue is extracted with acetone. The acetone extract is filtered and evaporated to give 4 g of a residue containing 90.7% (74.5% yield) citric acid and the balance, water.

EXAMPLE 12

A 1:1 mixture of dl-isocitric acid lactone and dl-alloisocitric acid lactone, 28.7 g (60.6% purity; balance, water), is dissolved in 500 mls of water. Calcium hydroxide, 65 g (0.85 mole), is added. This brings the pH to 11.8 and produces a mixture of the calcium salts of dl-isocitric acid and dl-alloisocitric acid together with free calcium hydroxide. The resulting mixture is stirred and heated for 6 hours in a Parr pressure reactor at a temperature of 200° C. The reaction mixture is then cooled, slurried with excess cation exchange resin and poured onto a column of additional cation exchange resin. After washing the resin thoroughly with water, the eluate including the washings are evaporated in vacuo to give a 20 g residue containing 83.2% (95.5% yield) of citric acid, 2.8% succinic acid and the balance, mainly water.

EXAMPLE 13

A mixture of 21.9 g of trans-aconitic acid, 3.6 g of di-isocitric acid lactone and 3.6 g of dl-alloisocitric acid lactone is dissolved in 300 mls water. An excess of calcium hydroxide, 30.7 g (0.41 mole), is added. This brings the pH to 11.6 and produces a mixture of the calcium salts of trans-aconitic acid, dl-isocitric acid and dl-alloisocitric acid together with free calcium hydroxide. The resulting mixture is stirred and heated for 6 hours in a Parr pressure reactor at a temperature of 200° C. The reaction mixture is then cooled, slurried with excess cation exchange resin and poured onto a column of additional cation exchange resin. After washing the resin thoroughly with water, the eluate including the washings are evaporated in vacuo to give a 22.3 g residue containing 90.8% (95% yield) of citric acid, 3% succinic acid and the balance, mainly water.

EXAMPLE 14

Trans-aconitic acid, 52.2 g (0.30 mole) is dissolved in 300 mls of water. An excess of calcium hydroxide, 90 g (1.22 moles), is added (slowly). This brings the pH to 12.0 and produces a mixture of the calcium salt of trans-aconitic acid and free calcium hydroxide. The resulting mixture is stirred and heated for 5½ hours in a Parr pressure reactor at a temperature of 200° C. The reaction mixture is then cooled and neutralized (slowly) with 421 g of a 29% solution of sulfuric acid solution. After stirring the mixture for about 10 minutes, it is filtered to remove the precipitated CaSO$_4$. The filtrate is then evaporated in vacuo to give a 52 g residue of crude citric acid.

Purification and Identification of Citric Acid

A. The crude citric acid, 52 g, is dissolved in 300 mls of water. Calcium hydroxide, 18.5 g (0.25 mole), is added with stirring. After standing 1 hour, the mixture is filtered to collect the precipitate of the monocalcium salt of citric acid. After washing the precipitate with water, it is slurried with fresh water and a cation exchange resin and then poured onto a column of additional cation exchange resin. The eluate and washings are evaporated to dryness in vacuo to yield 26 g of purified citric acid.

B. Four grams of the purified citric acid from (A) above is dissolved in 400 mls of 1:1 (by volume) chloroform: acetone and concentrated partially to precipitate crystals of citric acid. The crystals are filtered and recrystallized from 300 mls of 1:1 (by volume) chloroform: acetone to give 2.5 g of pure synthetic citric acid, m.p. 149.8–152.7° C. A mixed melting point with authentic citric acid gave no depression of the melting point of the authentic sample. The NMR spectra (in D$_2$O) of the synthetic and authentic samples of citric acid are identical.

C. Ten grams of the purified citric acid from (A) above is dissolved in 200 mls of methanol containing 5 g of concentrated sulfuric acid and the mixture is refluxed for 6 hours. Calcium carbonate is then added to neutralize the surfuric acid and the resulting mixture is filtered to remove CaSO$_4$ and CaCO$_3$. The methanolic filtrate is evaporated and the resulting residue dissolved in chloroform and filtered. The chloroform filtrate is evaporated to dryness and the resulting residue is dissolved in hot benzene and filtered. The hot benzene filtrate is allowed to cool slowly to crystallize the product. Five grams of pure trimethyl citrate is collected by filtration. The melting point of the synthetic preparation is 76.6° C compared to 75.5–75.6 for authentic trimethyl citrate. A mixing melting point of a 1:1 mixture of the synthetic and authentic trimethyl citrates is 75.8° C. The NMR spectrum (in D$_2$O) and the mass spectrum of the synthetic trimethyl citrate are identical to the corresponding spectra of authentic trimethyl citrate.

What is claimed is:

1. A process for preparing calcium, magnesium and strontium salts of citric acid and mixtures thereof comprising the corresponding salt or mixture of salts of a tricarboxylic acid selected from the group consisting of cis-aconitic acid, trans-aconitic acid, isocitric acid, alloiso-citric acid and mixtures thereof, in an aqueous medium at a temperature of at least about 160° C and in the presence of an alkali metal hydroxide or an alkaline earth metal hydroxide selected from the group consisting of calcium hydroxide, magnesium hydroxide, strontium hydroxide and mixtures thereof.

2. The process of claim 1 wherein the salt of the tricarboxylic acid is the calcium salt.

3. The process of claim 2 wherein the alkaline earth metal hydroxide is calcium hydroxide.

4. The process of claim 3 wherein the reaction temperature is from about 160° C to about 300° C.

5. The process of claim 3 wherein the reaction temperature is from about 175° C to about 250° C.

6. The process of claim 5 wherein the tricarboxylic acid is trans-aconitic acid.

7. The process of claim 5 wherein the tricarboxylic acid is cis-aconitic acid.

8. The process of claim 5 wherein the tricarboxylic acid is a mixture of cis- and trans-aconitic acids.

9. The process of claim 5 wherein the tricarboxylic acid is isocitric acid.

10. The process of claim 5 wherein the tricarboxylic acid is alloisocitric acid.

11. The process of claim 5 wherein the tricarboxylic acid is a mixture of isocitric acid and alloisocitric acid.

12. The process of claim 5 wherein the tricarboxylic acid is a mixture of trans-aconitic acid, isocitric acid and alloisocitric acid.

13. The process of claim 5 wherein the tricarboxlic acid is a mixture of cis-aconitic acid, isocitric acid and alloisocitric acid.

14. The process of claim 5 wherein the tricarboxylic acid is a mixture of cis-aconitic acid, trans-aconitic acid, isocitric acid and alloisocitric acid.

15. The process of claim 1 containing the additional step of isolating citric acid from the reaction mixture by converting said alkaline earth metal salts of citric acid into citric acid and isolating said citric acid.

16. A process for preparing citric acid comprising the steps of reacting the calcium salt of a tricarboxylic acid selected from the group consisting of cis-aconitic acid, trans-aconitic acid, isocitric acid, alloisocitric acid and mixtures thereof, in an aqueous medium at a temperature of at least 160° C and in the presence of calcium hydroxide to form a reaction mixture, treating said reaction mixture to remove the calcium ions to form an aqueous solution of citric acid and then isolating the citric acid from said solution.

17. A process for preparing citric acid comprising the steps of:
i. reacting the calcium salt of a tricarboxylic acid selected from the group consisting of cis-aconitic acid, trans-aconitic acid, isocitric acid, alloisocitric acid and mixtures thereof, in an aqueous medium at a temperature from about 175° C to about 250° C in the presence of sufficient calcium hydroxide to adjust to pH of the aqueous medium to about 11.3 to about 12.5 to form a reaction mixture,
ii. treating said reaction mixture to remove the calcium ions and form an aqueous solution of citric acid, and
iii. isolating said citric acid from said solution.

* * * * *

UNITED STATES PATENT AND TRADEMARK OFFICE
CERTIFICATE OF CORRECTION

PATENT NO. : 4,056,567
DATED : November 1, 1977
INVENTOR(S) : Vincent Lamberti et al.

It is certified that error appears in the above-identified patent and that said Letters Patent are hereby corrected as shown below:

In the Specification:

Col. 1, line 47: "molcule" should be -- molecule --.

Col. 8, line 14: "Tnis" should be -- This --.

Col. 9, line 34: "di-isocitric" should be -- dl-isocitric --.

Col. 9, line 66: "di-isocitric" should be -- dl-isocitric --.

In the Claims:

Claim 1, Col. 11, line 6: "comprising the corresponding" should be -- comprising reacting the corresponding --.

Claim 17, Col. 12, line 32: "adjust to pH" should be -- adjust the pH --.

Signed and Sealed this

Twenty-first Day of February 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,056,567
DATED : November 1, 1977
INVENTOR(S) : Vincent Lamberti et al.

It is certified that error appears in the above-identified patent and that said Letters Patent are hereby corrected as shown below:

In the specification:

Col. 3, line 17: "be" should be -- do --.

Signed and Sealed this

Twenty-fourth Day of October 1978

[SEAL]

Attest:

RUTH C. MASON
Attesting Officer

DONALD W. BANNER
Commissioner of Patents and Trademarks